United States Patent
Chelly et al.

(10) Patent No.: US 6,575,158 B1
(45) Date of Patent: Jun. 10, 2003

(54) ENDOTRACHEAL TUBE GUIDE AND RELATED TRACHEOSTOMY SURGICAL PROCEDURE

(75) Inventors: Jacques Chelly, Houston, TX (US); Jeffrey Katz, Houston, TX (US); Thomas Smith, Alvin, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 08/867,748

(22) Filed: Jun. 3, 1997

(51) Int. Cl.[7] .............................................. A61M 16/00
(52) U.S. Cl. ............................. 128/200.26; 128/207.29; 128/207.14
(58) Field of Search ....................... 128/200.26, 207.14, 128/200.24, 207.15, 912, 911, DIG. 26, 207.29; 623/9, 23.64, 23.65, 23.67; 600/121, 186, 190, 194, 203; 606/96, 98, 108

(56) References Cited

U.S. PATENT DOCUMENTS

| | | | | |
|---|---|---|---|---|
| 460,987 A | * | 10/1891 | Olivieri ................. | 128/207.14 |
| 2,862,498 A | * | 12/1958 | Weekes ................. | 128/207.14 |
| 3,605,751 A | | 9/1971 | Gulling | |
| 3,957,055 A | | 5/1976 | Linder et al. | |
| 4,211,234 A | * | 7/1980 | Fisher .................... | 128/200.26 |
| 4,454,887 A | * | 6/1984 | Kruger .................. | 128/207.14 |
| 4,655,214 A | | 4/1987 | Linder | |
| 4,672,960 A | | 6/1987 | Frankel | |
| 4,683,879 A | | 8/1987 | Williams | |
| 4,685,457 A | * | 8/1987 | Donenfeld ............. | 128/207.14 |
| 4,865,586 A | * | 9/1989 | Hedberg ................ | 128/207.14 |
| 4,877,021 A | * | 10/1989 | Higer et al. ........... | 128/207.14 |
| 4,892,095 A | * | 1/1990 | Nakhgevany .......... | 128/200.26 |
| 4,919,126 A | | 4/1990 | Baildon | |
| 4,960,122 A | * | 10/1990 | Mizus .................... | 128/200.26 |
| 5,078,743 A | * | 1/1992 | Mikalov et al. ....... | 623/9 |
| 5,119,811 A | | 6/1992 | Inglis et al. | |
| 5,235,970 A | | 8/1993 | Augustine | |
| 5,245,992 A | | 9/1993 | Nye ....................... | 128/200.26 |
| 5,323,771 A | | 6/1994 | Fisher et al. .......... | 128/200.26 |

(List continued on next page.)

FOREIGN PATENT DOCUMENTS

| | | | | |
|---|---|---|---|---|
| GB | 2318297 | * | 4/1998 | |
| WO | 9319798 | * | 10/1993 | ............. 128/200.26 |
| WO | WO 93/24161 | * | 12/1993 | ............. 128/200.26 |

OTHER PUBLICATIONS

Singer et al., An Endoscopic Technique for Restoration of Voice After Laryngectomy, Annals of Otology, Rhinology and Laryngectomy, Nov./Dec. 1980, vol. 89, No. 6.*

Primary Examiner—Aaron J. Lewis
(74) Attorney, Agent, or Firm—Duane Morris LLP

(57) ABSTRACT

An ET guide is provided which is preferably made of polytetrafluoroethylene (PTFE), also known as Teflon®. The distal end is of a reduced profile so that the guide can be left in place, with the ET removed in the operating room just prior to a tracheostomy. If for any reason problems are encountered in the tracheostomy procedure, the guide of the present invention, having been left in after the removal of the ET, can facilitate a reinsertion of the ET to avoid danger to the patient from a decrease in oxygen saturation. At the same time, the reduced distal profile allows the guide to remain in place during the tracheostomy procedure without obstructing the area of the incision for the tracheostomy. The guide can remain in place until the tracheostomy is successfully concluded, at which point it can be optionally removed. Leaving the guide in position as the tracheostomy is being conducted facilitates reinsertion of the ET which is routinely taken out in the operating room prior to the onset of the tracheostomy. In the preferred design, the guide has a circular cross-section until its distal end, which is a reduced-thickness, flattened segment of a predetermined length at the distal portion of the guide.

18 Claims, 1 Drawing Sheet

U.S. PATENT DOCUMENTS

| | | |
|---|---|---|
| 5,329,921 A | 7/1994 | Socaris et al. |
| 5,353,787 A | 10/1994 | Price |
| 5,429,127 A | 7/1995 | Kolobow |
| 5,507,279 A | 4/1996 | Fortune et al. |
| 5,546,936 A | 8/1996 | Virag et al. |
| 5,590,647 A * | 1/1997 | Nye ...................... 128/207.14 |
| 5,720,275 A * | 2/1998 | Patil et al. ............. 128/200.26 |
| 5,996,582 A * | 12/1999 | Turnbull ................ 128/207.29 |

* cited by examiner

ENDOTRACHEAL TUBE GUIDE AND RELATED TRACHEOSTOMY SURGICAL PROCEDURE

FIELD OF THE INVENTION

The field of this invention relates to endotracheal tube guides and their use in related tracheostomy procedures.

BACKGROUND OF THE INVENTION

Prior to delivery to the operating room, certain types of trauma patients are frequently intubated with endotracheal tubes (ETs) which are inserted into the trachea via a guide. Several issued U.S. patents deal with techniques of insertion of guides and ETs. Such patents are U.S. Pat. Nos. 4,672,960; 5,507,279; 5,235,970; 3,957,055; 4,892,095; and 4,655,214. Various designs of ETs have been used, as well as guides for such tubes. Of general interest in the area of ET and guide construction are U.S. Pat. Nos. 4,685,457; 5,329,921; 4,683,879; 4,919,126; 3,605,751; 5,119,811; 5,429,127; 5,353,787; and 5,546,936.

Thus, while guides have been used to insert ETs, when the patient is delivered to the operating room for surgery, the ET is typically removed as an incision is made in the trachea for insertion of the tracheal tube. The guide for the ET has already been removed prior to delivery of the patient to the operating room as part of the insertion procedure for the ET. Accordingly, in the past, if difficulties developed with the access to the trachea for insertion of the tracheal tube, it became necessary to reinsert the ET to prevent a decrease in oxygen saturation in the patient which could potentially lead to cardiac and brain damage, irreversible organ failure, or death.

Prior designs of airway guides have been sufficiently bulky so as to prevent their continuing use as a guide should reintubation with an ET be required during the tracheostomy procedure. Without the guide in place after removal of the ET during a tracheostomy procedure, there exists a risk that the ET will not be smoothly reinsertable into the patient after it has originally been withdrawn. This can occur because of inflammation caused by trauma which has been exacerbated with time and other conditions such that the initial removal of the guide for the ET, followed by removal of the ET during the tracheostomy, will preclude a quick reinsertion of the ET guide, followed by the ET, in a timely manner into the patient's trachea.

Accordingly, to address the potential risks to some patients where difficulty is encountered in the tracheostomy procedure, the apparatus and method of the present invention have been devised. The objective of the invention is to provide a guide having a suitable distal profile so as to facilitate the subsequent tracheostomy procedure without undue obstruction in the trachea. With the provision of such an airway guide, a procedure of the present invention has been developed so that the guide may be left in the trachea after removal of the ET at the onset of the tracheostomy procedure. A further object of the apparatus and method of the invention is to provide a guide made of a material with a low coefficient of friction such that on its own and/or in conjunction with body fluids, it can facilitate a rapid reinsertion of the ET. Yet another object of the invention is to provide a design for the guide which facilitates its sterilization for reuse.

Some prior designs (Eschmann) have incorporated a composite structure for the guide. In this design, the interior of the guide is made from a core made of a woven material, coated with a plastic material. However, in use, the plastic coating developed cracks which exposed the woven substrate and made sterilization of such designs a questionable procedure. Guides or stylets made with or without a lumen and having a constant cross-sectional area have also been employed, using polyvinylchloride (PVC). Accordingly, another object of the present invention is to provide a guide made from preferably a unitary material which has good lubricity and which can be reliably sterilized, yet at the same time be simply fabricated or molded into the desired shape so it can remain in place without getting in the way during a tracheostomy.

SUMMARY OF THE INVENTION

An ET guide is provided which is preferably made of polytetrafluoroethylene (PTFE), also known as Teflon®. The distal end has a reduced profile so that the guide can be left in place, with the ET removed in the operating room just prior to a tracheostomy. If for any reason problems are encountered in the tracheostomy procedure, the guide of the present invention, having been left in after the removal of the ET, can facilitate a reinsertion of the ET to avoid danger to the patient from a decrease in oxygen saturation. At the same time, the reduced distal profile allows the guide to remain in place during the tracheostomy procedure without obstructing the area of the incision for the tracheostomy. The guide can remain in place until the tracheostomy is successfully concluded, at which point it can be optionally removed. Leaving the guide in position as the tracheostomy is being conducted facilitates reinsertion of the ET which is routinely taken out in the operating room prior to the onset of the tracheostomy. In the preferred design, the guide has a circular cross-section until its distal end, which is a reduced-thickness, flattened segment of a predetermined length at the distal portion of the guide.

DETAILED DESCRIPTION OF THE DRAWINGS

DETAILED DESCRIPTION OF THE PREFERRED EMBODIMENT

Figure 1:
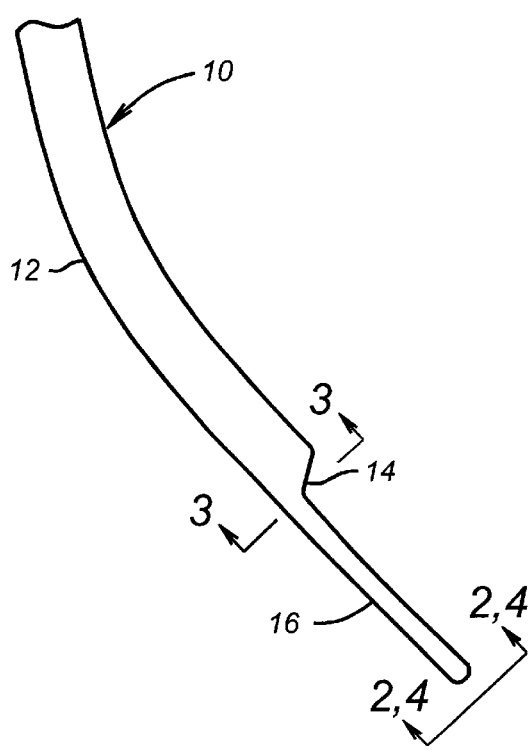
FIG. 1 illustrates a sectional elevational view of the guide, showing the reduced profile distal segment.

The airway guide 10 is illustrated in FIG. 1. It has a preferably elongated body having a preferably rounded cross-section, although other shapes can be used. The diameter of the rounded portion of the body 12 varies depending on whether the guide is to be used for adults or children. The preferred size for adults is ³⁄₁₆" and the preferred size for children is ⅛". A transition occurs at transition point 14 where the profile of the guide 10 changes from the preferably rounded segment 12 to a preferably flat segment 16. Other lower-profile distal segment cross-sections can be used as long as they do not interfere with the tracheostomy procedure when left in place. The preferred length of the flat distal segment 16 varies with the application, but in general for adults is approximately 3–5", with the overall length of the guide 10 being approximately preferably 39", although other lengths can be used without departing from the spirit of the invention.

Figure 2:
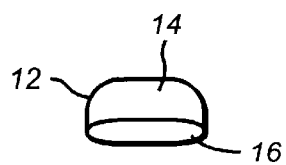
FIG. 2 is an end view taken along lines 2—2 of FIG. 1.
Figure 3:
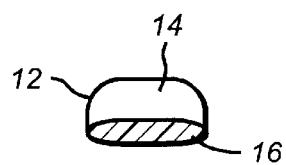
FIG. 3 is a sectional view taken along lines 3—3 of FIG. 1.
Figure 4:
FIG. 4 is an alternative embodiment, showing a different placement of the reduced-diameter section at the distal end of the guide.

FIG. 2 illustrates the change in cross-section by illustrating a generally oblong profile when looking at the end of the flattened segment 16. FIGS. 3 and 4 illustrate that the segment 16 can be made alternatively to jut out from a lower portion of the body 12, as shown in FIG. 3, or from a middle portion of the body 12 such that the center of the flattened portion 16 is in alignment with the longitudinal axis of the rounded portion of the guide 10 at body 12. Although FIGS. 3 and 4 show the reduced profile segment to be relatively flat on opposing sides, other reduced-profile shapes for segment 16 are within the purview of the invention. The function of the reduced-profile segment 16 is to allow it to remain in the trachea 18 (see FIG. 5) during the tracheostomy procedure without being in the way. Thus, as shown in FIG. 5, the guide 10 is disposed in the trachea 18 with segment 16 located in the area of the incision to be made in the trachea 18.

Figure 5:
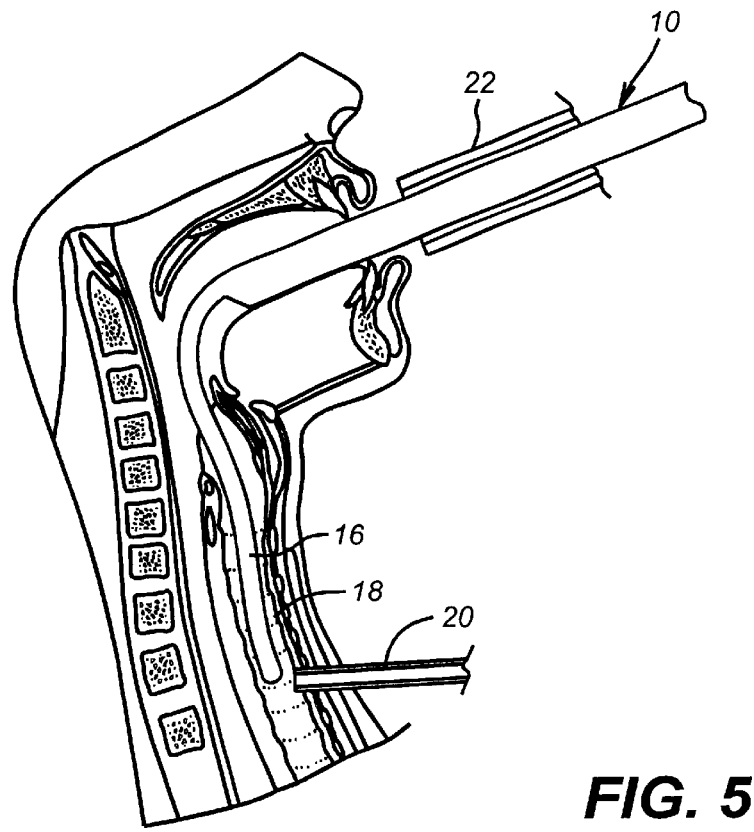
FIG. 5 is a sectional elevational view showing the guide in place, with the ET in position over the guide for a potential reinsertion as the tracheostomy procedure begins in a typical operating room.

A tracheostomy tube 20 is schematically illustrated in FIG. 5. Prior to attempting to insert the tube 20, an incision is made in the trachea, with the guide 10 in position as shown in FIG. 5, and the ET 22 having been removed from the trachea 18 in the operating room. The ET 22 may remain on the extending portions of the guide 10 so that it may be available for rapid reinsertion should problems develop with the tracheostomy procedure. Alternatively, the ET 22 can be completely removed from the guide 10 during the tracheostomy procedure but kept nearby in the event that it is needed.

The advantages of the apparatus and method of the present invention are now made clear to a person of ordinary skill in the art. The prior procedure for performance of a tracheostomy involved generally an intubated patient that had an ET 22 inserted into the trachea 18 over a guide of some type and the guide was then removed. However, when that patient was brought into the operating room and a tracheostomy was required, the ET 22 would be removed before the tracheostomy procedure would begin. However, if difficulties developed during the tracheostomy procedure, the trachea 18 would have to be reopened by a reinsertion of the ET 22. For some patients, trauma-induced inflammation or inflammation induced by other reasons presented difficulties in reinsertion of the ET 22. At the same time, prior designs for airway guides did not permit leaving the guides in the trachea 18 because they would be in the way of the tracheostomy procedure.

Prior designs of airway guides also made insertion of ETs difficult in that the materials of construction of the guides were not lubricious and created significant amounts of resistance in advancement of the ET 22 over the prior design guides. Additionally, composite guides, such as plastic-coated fiber, also presented logistical problems in effective sterilization due to crevice formation which could trap foreign materials and make the sterilization procedure somewhat uncertain.

Accordingly, the guide 10 of the present invention is preferably made from polytetrafluoroethylene (PTFE), or Teflon®. Teflon® is a material that is easy to work with and form into a desired shape. It has sufficient strength to be easily advanced while retaining sufficient flexibility to be guided into the trachea 18. Teflon® is also very lubricious, making it easier to advance into the trachea, as well as easier to advance the ET 22 over it. The reduced-profile distal section allows the guide 10 to remain in position during the tracheostomy. With the guide 10 in position during tracheostomy, should any problems develop in the tracheostomy, the ET 22 can be quickly advanced over the guide 10 which has remained in place due to its low distal profile. Thus, risk to the patient from lack of access to the airway is eliminated, while at the same time the presence of the guide 10 with its reduced-profile distal segment 16 in the trachea 18 does not impede the tracheostomy procedure.

The use of Teflon® for the guide 10 allows it to better hold its shape. The low-profile distal segment 16 is preferably offset from the centerline of the cylindrical portion that is proximal to it. However, other orientations are within the purview of the invention. The preferred shape for the distal segment 16 encompasses a low profile having preferably two parallel sides and rounded edges. However, other shapes can be used, such as oval, elliptical, and rectangular, to name a few. Teflon® material easily lends itself to the formation of a variety of cross-sectional shapes for the guide 10, particularly the distal segment 16. The important thing is that the distal segment be sufficiently strong so as to resist, without fracture, applied bending stresses which are encountered during insertion of the guide 10, while at the same time presenting a reduced profile and preferably at an offset location so that the distal segment 16 can be left in place in the trachea 18 while presenting the least amount of interference possible to the tracheostomy procedure.

The guide 10 can be reusable or it can be disposable. A lubricant can be applied to the guide 10; however, if Teflon® is used, body fluids are generally sufficient to assure lubrication to facilitate advancement of the guide 10. While Teflon® is the preferred material for the guide 10, other plastic materials can also be used, such as PVC or other flexible metallic or nonmetallic materials.

It can clearly be seen that with the apparatus of the present invention, protection of the airway is available, making it possible for quick reintubation using an ET 22 if for any reason the tracheostomy tube 20 cannot be readily and quickly inserted into the trachea 18 in the operating room. Should the occasion arise, the guide 10, with its low-profile distal segment 16, not only facilitates normal tracheostomies without interference, but also is there for a back-up should the ET 22, which has been removed upon admittance of the patient into the operating room, need to be reinserted quickly.

The foregoing disclosure and description of the invention are illustrative and explanatory thereof, and various changes in the size, shape and materials, as well as in the details of the illustrated construction, may be made without departing from the spirit of the invention.

What is claimed is:

1. A method for performing a tracheostomy, comprising:
   a. leaving an endotracheal tube guide in the trachea unattached to an endotracheal tube;
   b. creating an incision into the trachea; and
   c. attempting to insert a tracheostomy tube through said incision.

2. The method of claim 1, further comprising:
   inserting an endotracheal tube over said guide if said attempt to insert said tracheostomy tube is unsuccessful.

3. The method of claim 1, further comprising:
   using an endotracheal tube guide having a reduced profile on its distal end.

4. The method of claim 3, further comprising:
   using a tube guide which transitions to a relatively flat distal segment.

5. The method of claim 4, further comprising:

using a tube guide which transitions from a substantially round proximal profile to said relatively flat distal segment.

6. The method of claim 5, further comprising:

using a tube guide made of a single material.

7. The method of claim 6, further comprising:

using a tube guide made of PTFE.

8. The method of claim 7, further comprising:

sterilizing said guide for reuse.

9. The method of claim 7, further comprising:

disposing of said guide after an initial use.

10. The method of claim 2, further comprising:

using an endotracheal tube guide having a reduced profile on its distal end.

11. The method of claim 10, further comprising:

using a tube guide which transitions to a relatively flat distal segment.

12. The method of claim 11, further comprising:

using a tube guide which transitions from a substantially round proximal profile to said relatively flat distal segment.

13. The method of claim 11, further comprising:

using a tube guide made of PTFE.

14. The method of claim 11, further comprising:

sterilizing said guide for reuse.

15. The method of claim 11, further comprising:

disposing of said guide after an initial use.

16. An endotracheal tube guide for guiding an endotracheal tube over it, if needed, while making an incision into a trachea for a tracheostomy comprising:

an elongated body comprising a proximal segment and a distal segment, said distal segment having a solid cross-section;

said distal segment having a smaller cross-section area that said proximal segment which is sufficiently small so as to allow said distal segment to remain in the trachea, clear of the incision location, while a tracheostomy procedure is performed; and said proximal segment has a rounded cross-section and said distal segment has a narrower, flattened cross-section.

17. An endotracheal tube guide for guiding an endotracheal tube over it, if needed, while making an incision into a trachea for a tracheostomy, comprising:

an elongated body comprising a proximal segment and a distal segment, said distal segment having a solid cross-section;

said distal segment having a smaller cross-section area that said proximal segment which is sufficiently small so as to allow said distal segment to remain in the trachea, clear of the incision location while a tracheostomy procedure is performed;

said proximal and distal segments of said body are solid in cross-section;

said proximal and distal segments are made of a single lubricious material;

said proximal and distal segments are made of PTFE; and said proximal segment has a rounded cross-section and said distal segment has a narrower, flattened cross-section.

18. The guide of claim 17, wherein:

said distal segment has a longitudinal axis, said proximal segment further comprises a longitudinal axis which is misaligned from said longitudinal axis of said distal segment.

* * * * *